(12) United States Patent
Walker (10) Patent No.: US 10,413,414 B2
(45) Date of Patent: Sep. 17, 2019

(54) REPLICA GUIDED MOTION KNEE

(71) Applicant: Peter Stanley Walker, New York, NY (US)

(72) Inventor: Peter Stanley Walker, New York, NY (US)

(73) Assignee: NEW YORK UNIVERSITY, New York, NY (US)

(*) Notice: Subject to any disclaimer, the term of this patent is extended or adjusted under 35 U.S.C. 154(b) by 0 days.

(21) Appl. No.: 15/205,554

(22) Filed: Jul. 8, 2016

(65) Prior Publication Data

US 2017/0020674 A1 Jan. 26, 2017

Related U.S. Application Data

(60) Provisional application No. 62/189,809, filed on Jul. 8, 2015.

(51) Int. Cl.
*A61F 2/38* (2006.01)
*A61F 2/30* (2006.01)

(52) U.S. Cl.
CPC .............. *A61F 2/3859* (2013.01); *A61F 2/38* (2013.01); *A61F 2/389* (2013.01); *A61F 2002/30266* (2013.01); *A61F 2002/30327* (2013.01); *A61F 2002/30621* (2013.01); *A61F 2002/30934* (2013.01)

(58) Field of Classification Search
CPC .......... A61F 2/38; A61F 2/3859; A61F 2/389; A61F 2002/30934; A61F 2002/30621
See application file for complete search history.

(56) References Cited

U.S. PATENT DOCUMENTS 7,309,362 B2 * 12/2007 Yasuda ..................... A61F 2/38
623/20.31

OTHER PUBLICATIONS

International Preliminary Report on Patentability; The International Bureau of WIPO; Geneva, Switzerland; Jan. 9, 2018.

* cited by examiner

*Primary Examiner* — Brian Dukert

(57) ABSTRACT

A total knee replacement, comprising a femoral and a tibial component in articulating contact that can restore normal joint function. The articulation between the two components is controlled by four guide surfaces.

14 Claims, 9 Drawing Sheets

*Posterior* ←——→ *Anterior*

REPLICA GUIDED MOTION KNEE

CROSS-REFERENCE TO RELATED APPLICATIONS

This non-provisional US patent application claims the benefit of priority from U.S. provisional patent application No. 62/189,809, filed 8 Jul. 2015. The disclosure of each such application is hereby incorporated by reference in its entirety where appropriate for teachings of additional or alternative details, features, and/or technical background, and priority is asserted from each.

BACKGROUND OF THE INVENTION

The replacement of a knee joint may become necessary as a result of malformation, disease or injury. A major goal of a total knee replacement (TKR) is to restore normal knee joint operation thereby allowing the patient to carry out required functional activities without experiencing pain or instability. There is evidence that this goal can be achieved if the kinematics of the knee after the procedure are similar to the kinematics when the patient's knee was in a healthy condition, and if the shape of the components blends closely to the anatomical shapes of the femur and tibia. The kinematics can be described by two parameters. Firstly, the neutral path of motion of the femur with respect to the tibia during the flexion range when there is only a compressive force acting in the direction of the long axis of the tibia. Secondly, the laxity about the neutral path when an anterior-posterior shear force or internal-external torque are superimposed on the compressive force. In regard to the shape, the components should approximate the shapes of the average femur and tibia, The applicant has recognized this need and has developed a total knee replacement that accomplishes these goals.

FIELD OF INVENTION

The present invention generally relates to medical prosthetic devices and their operation such as (without limitation) total knee replacement.

SUMMARY OF THE INVENTION

In embodiments there is presented a total knee replacement comprising a femoral component having a femoral bearing surface, the femoral bearing surface comprising a lateral section located adjacent, in a medial-lateral direction, to an central section that is adjacent, in a medial-lateral direction, to a medial section, wherein coronal and sagittal cross-sections of the lateral and medial sections are convex, and central section has a convex sagittal cross section and a concave coronal cross section; and a tibial component with a tibial bearing surface in articulating contact with the femoral bearing surface, the tibial bearing surface comprising a lateral segment located adjacent, in a medial-lateral direction, to an central segment that is adjacent, in a medial-lateral direction, to a medial segment, wherein sagittal cross section of the lateral segment is approximately flat and coronal cross section is concave, a sagittal and coronal cross sections of the medial segment are concave, and the sagittal cross section of the central segment is concave while the coronal cross section is convex.

The embodiments of the total knee replacement, may further provide that coronal cross-sections of the lateral femoral sections are defined by a first radius, and coronal cross-sections of the lateral tibial segments are defined by a second radius, the first radius is smaller than the second radius; coronal cross-sections of the medial femoral sections are defined by a third radius, and coronal cross-sections of the lateral tibial segments are defined by a fourth radius, the third radius is smaller than the fourth radius; sagittal cross-sections of the medial femoral sections are defined by a fifth radius, and sagittal cross-sections of the medial tibial segments are defined by a sixth radius, the fifth radius is smaller than the sixth radius; sagittal cross-sections of the central femoral sections are defined by a seventh radius, and sagittal cross-sections of the central tibial segments are defined by a eighth radius, the seventh radius is smaller than the eighth radius; and coronal cross-sections of the central femoral sections are defined by a ninth radius, and sagittal cross-sections of the central tibial segments are defined by a tenth radius, the tenth radius is smaller than the ninth radius.

The embodiments of the total knee replacement, may also provide that the lateral section of the femoral component comprises lateral condyle and the medial section of the femoral component comprises a medial condyle, the sagittal cross section of each of the medial condyle and the lateral condyle has a constant sagittal radius over the arc of flexion from zero to approximately 160 degrees flexion, and from the anterior extreme to the distal end for 0 degrees flexion, the sagittal section slopes upwards by an average of 12 degrees on the lateral side and 20 degrees on the medial side.

The embodiments of the total knee replacement, may also provide that the sagittal cross-section of the flat lateral segment of the tibial component is sloped by approximately 7 degrees relative to a transverse plane descending in the posterior direction; the sagittal cross-section of the flat lateral section of the femoral component is sloped by approximately 12 degrees relative to a transverse plane descending in the posterior direction; the sagittal cross-section of the flat central segment of the tibial component is sloped posteriorly by approximately 12 degrees relative to a transverse plane descending in the posterior direction; and the sagittal cross section of the flat medial segment of the tibial component is sloped by approximately 20 degrees relative to a transverse plane descending in the posterior direction.

The embodiments of the total knee replacement may also require that a radius of a sagittal cross-section of a posterior lip of the tibial component is equal to, or up to 2 mm greater than, the radius of a sagittal cross-section of the femoral condyles.

The embodiments of the total knee replacement may also require a patella bearing surface that has a depth of at least 7 mm and a side slope angle of 23 degrees, and a decreasing sagittal radius with increasing flexion angle from approximately 16 mm to 14 mm.

The embodiments of the total knee replacement may also require that the section of the femoral bearing surface smoothly blends into each the adjacent sections, and each the segment of the tibial bearing surface smoothly blends into each the adjacent segments.

The embodiments of the total knee replacement may also require that the central region of the lateral tibial surface is sloped posteriorly in the sagittal plane by 5-8 degrees relative to a transverse plane and is configured to produce posterior femoral displacement by gravity.

The embodiments of total knee replacement may also require that a center of the sagittal cross-section of a posterior portion of the lateral femoral condyle, and a center of the sagittal cross-section of a posterior portion of the medial femoral condyle, and a center of the sagittal cross-section of the central section, of the femoral component are collinear, and that the sagittal cross-sections of the lateral and medial condyles comprise condylar arcs of constant radius from 0 degrees flexion to maximum flexion, and that the sagittal cross-section of the central section comprise a central arc of constant radius smaller than the condylar arc wherein radius of the condylar arc decreases after approximately 60 degrees flexion. Maximum flexion is approximately 135 degrees.

BRIEF DESCRIPTIONS OF DRAWINGS

Embodiments of the invention are illustrated in the accompanying drawings in which:

FIG. 2a is a medial-anterior view of an embodiment of the femoral and tibial components relatively oriented for 0 degrees flexion angle while FIG. 2b is a medial-posterior view.

FIG. 3a is a medial anterior view of an embodiment of the femoral and tibial components relatively oriented for 90 degrees flexion angle while

DETAILED DESCRIPTION OF THE INVENTION

The total knee replacement (TKR), herein disclosed in embodiments, is designed for application when both of the cruciate ligaments are resected. This type of TKR is the most commonly used today, and allows for ease of surgery and consistency of technique. This requires that the stability normally provided by the cruciate ligaments must be provided by guiding surfaces that come in contact between the femoral and tibial components. The disclosed TKR employs such guiding surfaces, but additionally employs the force of gravity to activate the TKR thereby achieving the required kinematic characteristics. The required kinematics can be summarized as follows: for the neutral path, as the knee is flexed, the lateral contact point displaces posteriorly to the posterior of the tibia, while the medial contact point displaces only a few millimeters, most occurring after 90 degrees flexion. Throughout flexion there is laxity in both anterior-posterior (AP) and internal-external rotation. The lateral laxity is much larger than the medial and occurs primarily by the contact point displacing anteriorly. On the other hand the medial contact point displaces posteriorly. The medial side is very stable to anterior displacement. The Guiding Surfaces of the invention guide such a motion, a key factor being that the motion guidance occurs when there is compressive knee acting across the joint, together with varying amounts of shear force and rotational torque.

Laxity of an anatomical joint may be defined as slackness or looseness of the joint. For purposes of this application, laxity may be provided and quantified as the degree of non-conformity between two contacting surfaces wherein the non-conformity permits the displacement of one surface with respect to the other in response to the application of a shear force.

Figures 1A, 1B, 1C:
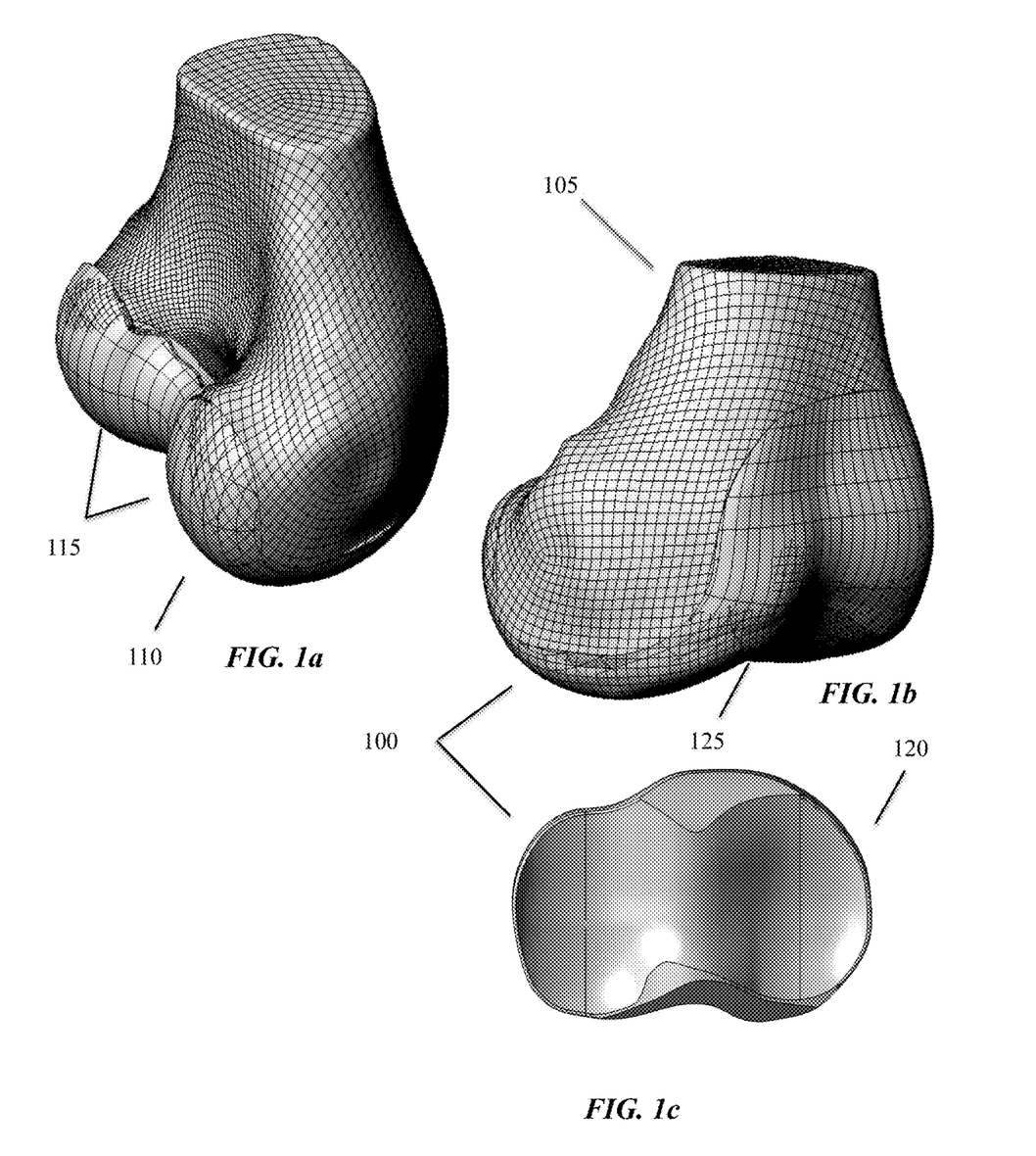
FIG. 1a is a medial-posterior view of an embodiment of the TKR comprising a femoral component, affixed to a femur, and a tibial component showing the femoral component attached to the distal extreme of a femur.
FIG. 1b presents a medial anterior view of the mounted femoral component.
FIG. 1c presents a transverse view of the proximal surface of the tibial component.

As shown in FIGS. 1a, 1b, and 1c, the TKR 100 is comprised of a femoral component 110 and a tibial component 120. FIG. 1a is a medial-posterior view showing the femoral component attached to the distal extreme of a femur 105. FIG. 1b presents a medial anterior view of the mounted femoral component. FIG. 1c presents a transverse view of the proximal surface of the tibial component. The distal bearing surfaces 115 of the femoral component 110 are derived by using an average anatomical femur shape (AAFS) as a template. The AAFS may be obtained by taking the average of multiple MRI scans and/or CT scans, of both normal knees and arthritic knees. The distal bearing surfaces 115 of the femoral component 110 differ from the AAFS in that the patella bearing surface 125 extends distally and posteriorly. This extended patella bearing surface 125 acts as an intercondylar guiding surface (IGS). As an added benefit, the extended patella bearing surface 125 provides continuous contact for the patella in high angles of flexion.

The peripheral shape of the tibial component 120 is the same as the periphery of an average tibia when it is resected horizontally to receive the tibial component. This component shape allows the various soft tissues including ligaments, capsule and muscles, to flow naturally around the implant surfaces. This will prevent pain from over-stretched soft tissues, and instability from too loose soft tissues. It will also allow for normal muscle mechanics.

Figures 2A, 2B:
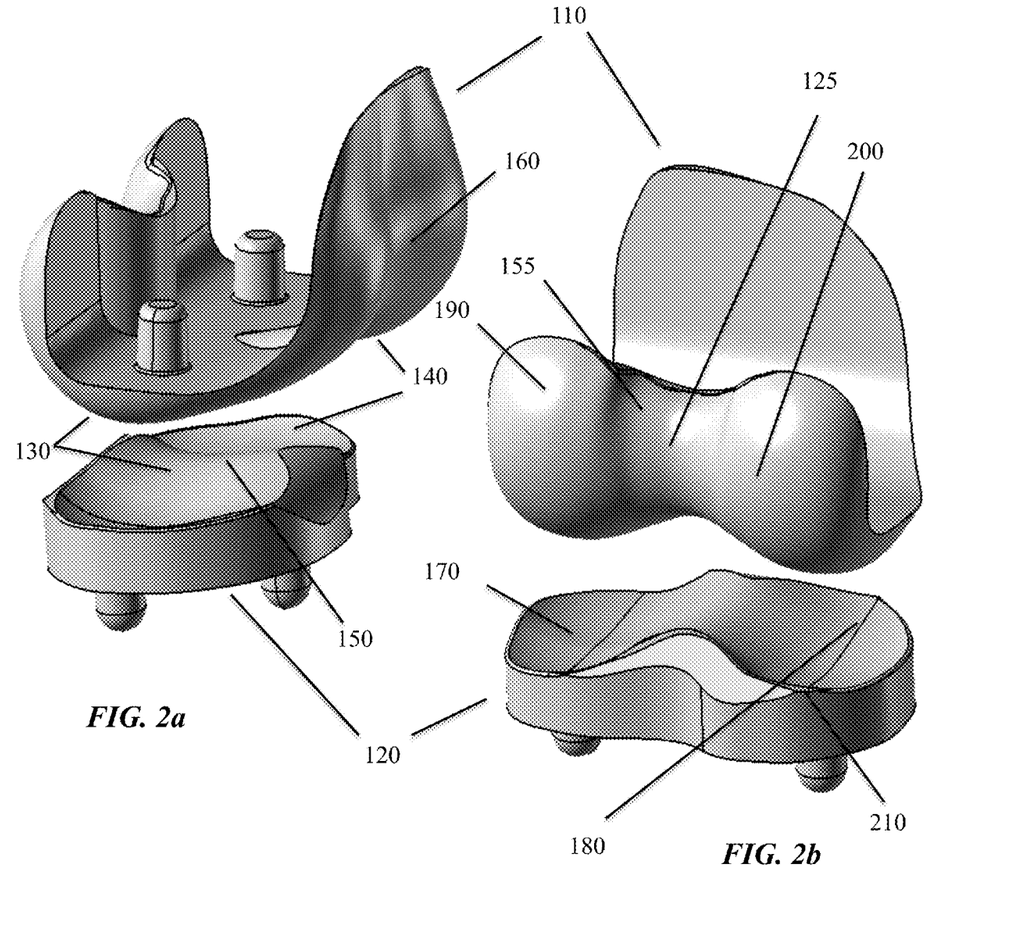
Figure 3A:
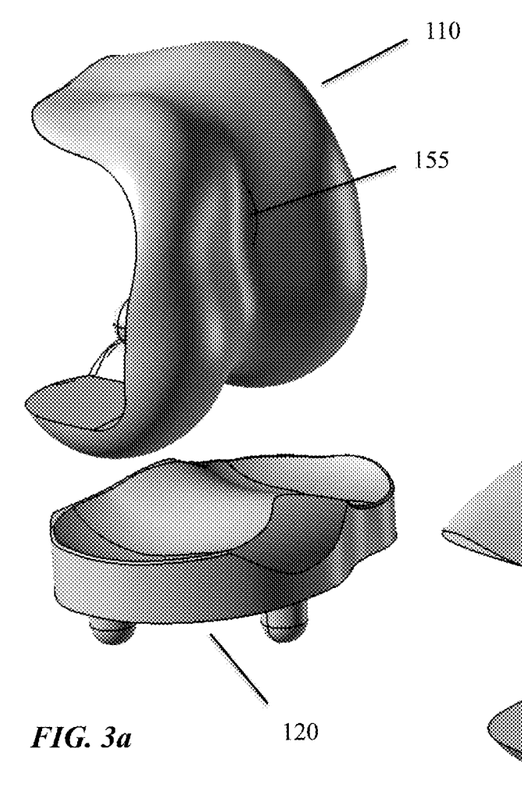
Figure 3B:
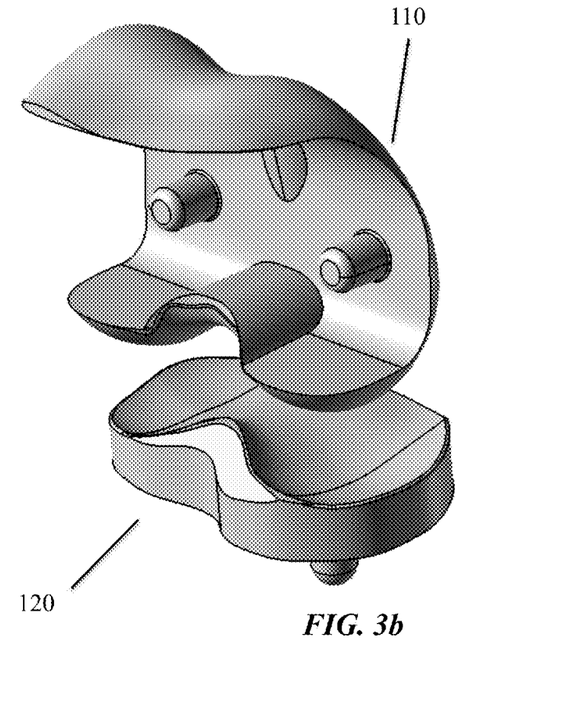
FIG. 3b is a medial-posterior view.

FIGS. 2a, 2b, 3a, and 3b illustrate exploded views of the femoral 110 and tibial 120 components, showing their relative orientation corresponding to 0 and 90 degree flexion, respectively. FIGS. 2a and 3a are medial anterior views while 2b and 3b are medial-posterior views. The femoral 110 and tibial 120 components comprise four distinct pairs of femoral and tibial guiding surfaces: 1) the medial bearing surfaces 130, 2) the lateral bearing surfaces 140, 3) the intercondylar surfaces 150, and 4) the patella-femoral surfaces 160. With regard to the patella-femoral surfaces 160, the continuous surface of the femur allows the patella to be in complete contact with the patella bearing surface 125 even in high flexion. This feature avoids the catching or clicking or tilting which can occur with many present total knee designs where there is a central gap that comes into play after about 90 degrees flexion. The medial bearing surfaces 130, lateral bearing surfaces 140, and intercondylar surfaces 150, surfaces guide the motion, during flexion, in the required way. On the lateral side, the shallow tibial surface 170 provides progressive posterior femoral displacement with flexion. On the medial side of the tibial component 120, the steep anterior surfaces 180 limit anterior femoral displacement. The intercondylar surfaces 150 play the important role of controlling the posterior position of the femur on the tibia. The position of contact between the femoral component 110 and the tibial component 120 moves progressively posteriorly with flexion. On the lateral side, the slope of the tibial surface 170 induces a progressive downward displacement of the lateral femoral condyle 190 with flexion. The higher posterior lip 210 on the medial tibial surface restrains the medial femoral condyle 200.

Figure 4:
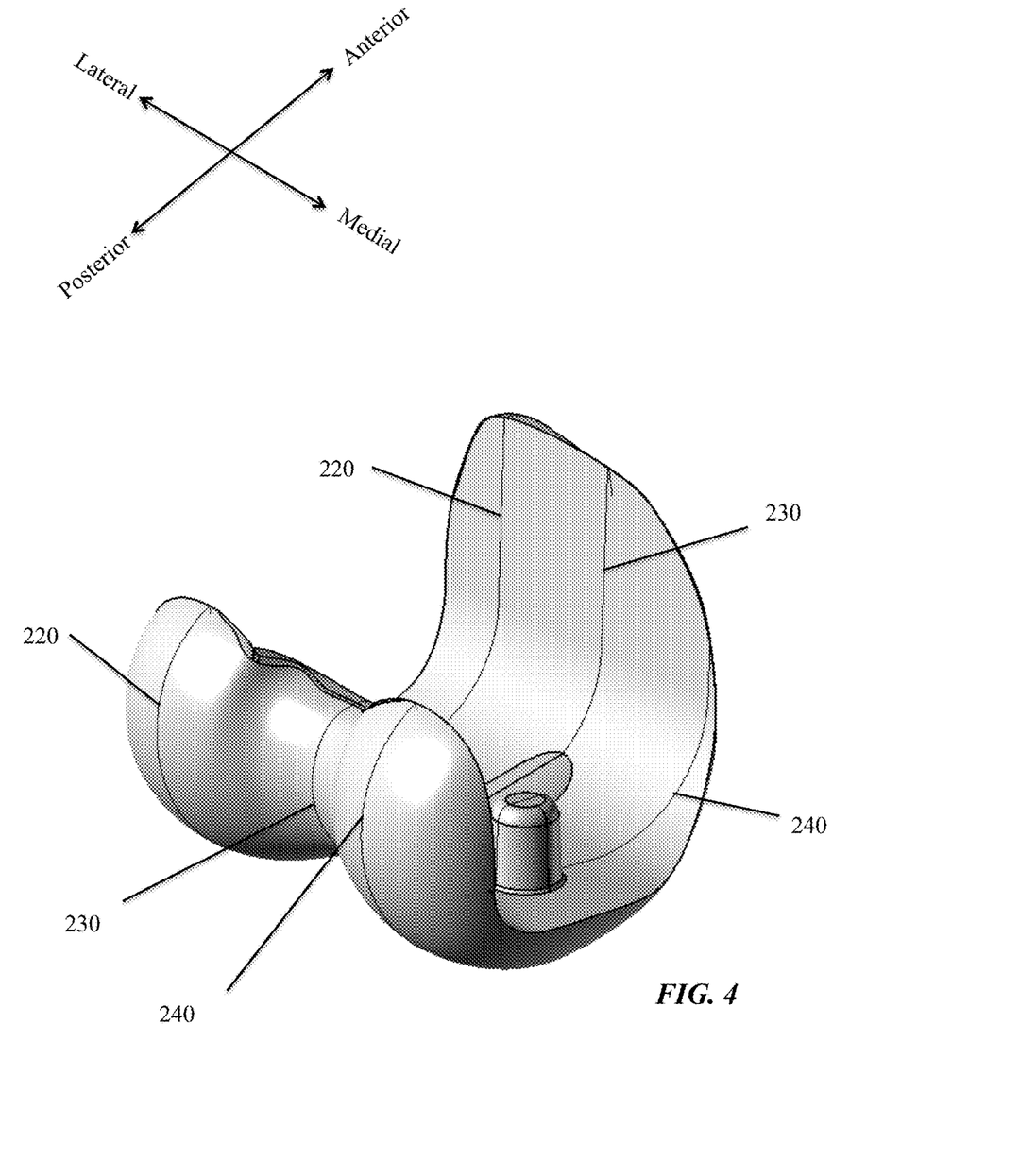
FIG. 4 is an embodiment of the femoral component illustrating the cutting planes that are employed to define the geometry of the contacts between the four distinct pairs of femoral and tibial guiding surfaces.

FIG. 4 illustrates the cutting planes for the sections of the femoral component 110 that are employed to define the geometry of the contacts between the four distinct pairs of femoral and tibial guiding surfaces 130, 140, 150, 160 of femoral 110 and. tibial 120 components. The cutting planes include the mid-lateral section 220, the central section 230, and the mid-medial section 240, The cutting planes can be extended to the component 120 thereby defining corresponding sections of the tibial component 120.

Figures 5, 6:
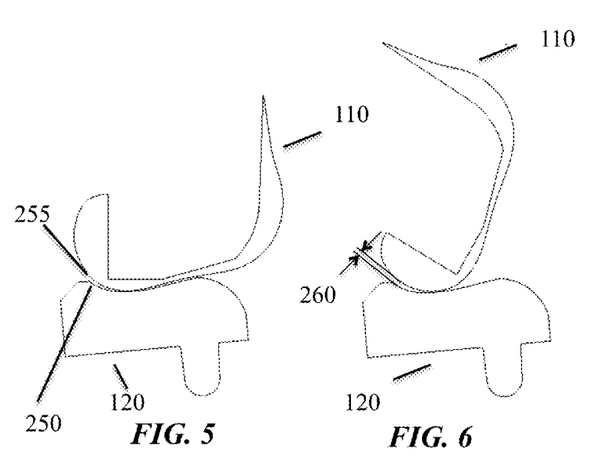
FIG. 5 is an embodiment of a central cross section of the intercondylar guiding surfaces for a 0 degree flexion angle.
FIG. 6 is an embodiment of a central cross section of the intercondylar guiding surfaces for a 60 degree flexion angle.
Figure 7:
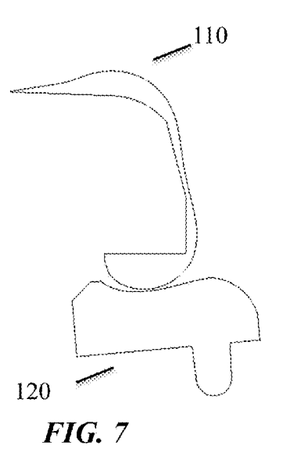
FIG. 7 is an embodiment of a central cross section of the intercondylar guiding surfaces for a 90 degree flexion angle.

Referring to FIGS. 5, 6, and 7, the central sections 230 of the intercondylar guiding surfaces (IGS) are shown for 0, 60 and 90 degrees flexion, respectively. The tibial component comprises a posteriorly located inter-condylar saddle 150. The distance 260 between the posterior lip 250, and the closest point on the femoral component surface 255 provides the required laxity for proper knee articulation. For 0 degree flexion, distance 260 should be approximately zero. For flexion angles of 60 and 90 degrees, distance 260 should be approximately 1 mm and 4 mm, respectively. It should be understood that these flexion angles are selected illustrate the operation of the joint and that the joints smoothly transition from one orientation to another over the full range of flexure from approximately −10 degrees to +160 degrees. From 0 to 60 degrees, the IGS surfaces prevent posterior displacement of the femur. After 60 degrees, there is progressively more displacement allowed. Most of this displacement occurs on the lateral side, because the lateral condyles have low constraint, compared with the medial condyles that have higher constraint.

Figure 8:
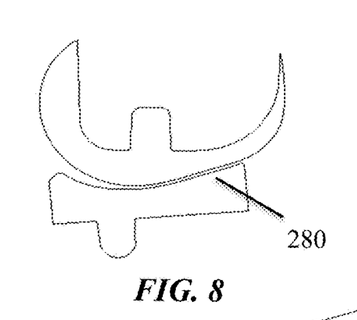
FIG. 8 is an embodiment of a mid-medial cross section of the intercondylar guiding surfaces for a 0 degree flexion angle.
Figure 9:
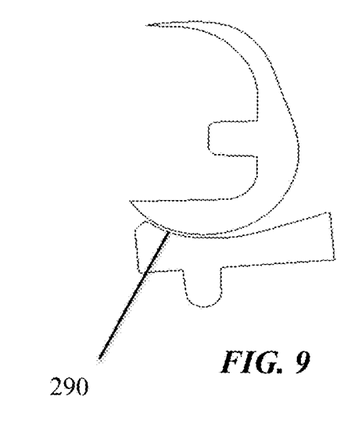
FIG. 9 is an embodiment of a mid-medial cross section of the intercondylar guiding surfaces for a 90 degree flexion angle.
Figure 10:
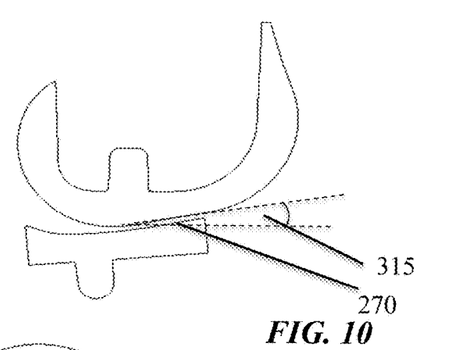
FIG. 10 is an embodiment of a mid-lateral cross section of the intercondylar guiding surfaces for a 0 degree flexion angle.
Figure 11:
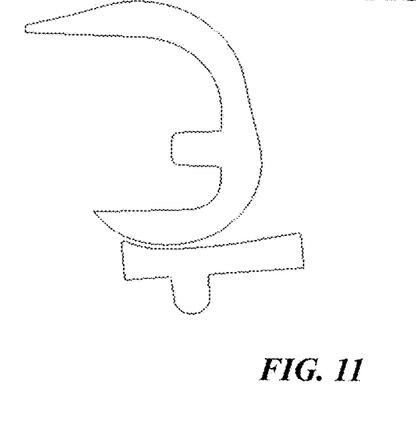
FIG. 11 is an embodiment of a mid-lateral cross section of the intercondylar guiding surfaces for a 90 degree flexion angle.
Figure 15:
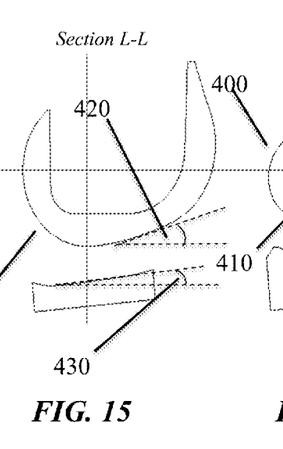
FIG. 15 is a sagittal view of section L-L of embodiments of the femoral and tibial components.

The mid-medial sections 240 are shown in FIGS. 8 and 9 for 0 degree and 90 degree flexion respectively. The mid-lateral sections 220 are shown in FIGS. 10 and 11 for 0 degrees and 90 degrees respectively. The relative constraint of anterior-posterior movement provided by the IGS surfaces can be seen. An important aspect of the lateral tibial surface is the sloped surface 270 of approximately 5 to 8 degrees, descending in the anterior to posterior direction relative to a transverse plane 315, and is approximately linear. The sloped lateral portion extends from anterior of the component towards the posterior of the component. The anterior starting point is preferentially between 0-12 mm from the anterior of the lateral section (FIG. 15) and the ending point is between 6-10 mm from the posterior of the lateral section (FIG. 15). When there is a compressive load across the knee, the lateral tibial condyle will displace down the slope until it is constrained elsewhere. The reason for this is that there is a component of the compressive force, acting down the line of the tibial surface. The medial surface behaves differently. Because of the steep anterior surfaces 280, anterior displacement of the femoral component 110 is limited. Posteriorly, there is only a small lax region before the posterior lip 290 of the tibia prevents further posterior displacement of the femoral component 110.

Figure 12:
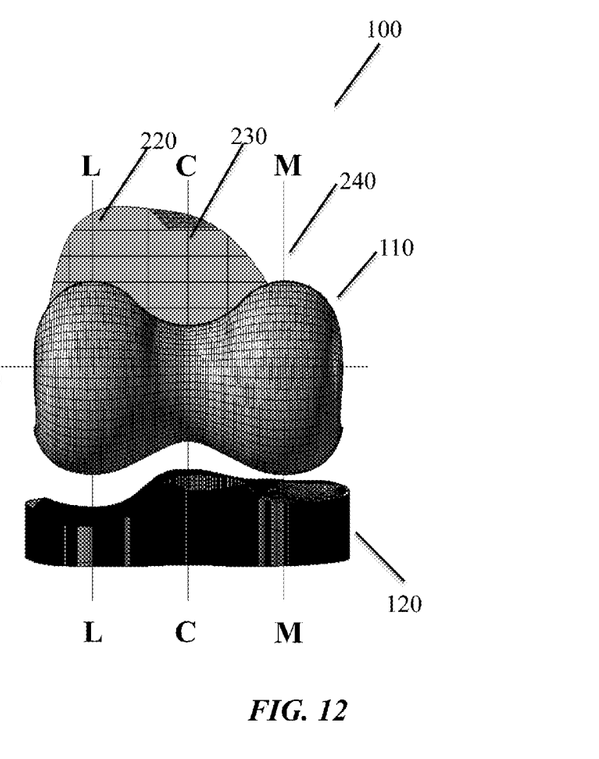
FIG. 12 is a posterior frontal plane view of an embodiment of the TKR comprising the femoral and tibial components and indicating the mid-lateral cut plane (L-L), the central cut plane (C-C), and the mid-medial cut plane (M-M).
Figure 13:
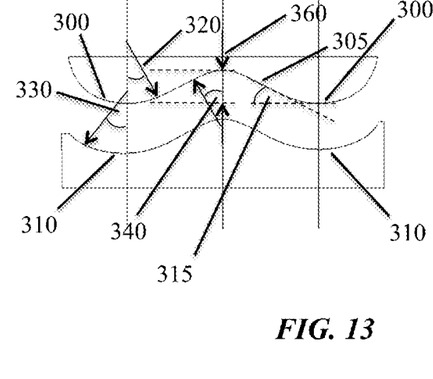
FIG. 13 is a posterior view of a cross section of an embodiment of the TKR, generated by a coronal cut plane.

FIG. 12 is a posterior frontal view of the TKR 100 comprising the femoral 110 and tibial 120 components and indicating the mid-lateral cut plane 220 (L-L), the central cut plane 230 (C-C), and the mid-medial cut plane 240 (M-M). FIG. 13 is a corresponding view of a frontal cross section generated by a coronal cut plane (V-V; see FIG. 14).

In an embodiment, the dimensions provided are suitable for a TKR appropriate for an average size male knee. The linear dimensions of the TKR may be scaled by a constant scaling factor for other knee sizes. In this case, the angles specified should be preserved. The horizontal spacing between the high points 300 on the femoral surface and the low points 310 on the tibial surface are spaced by approximately 48 mm (2×24 mm). The femoral radius 320 at those locations is approximately 22 mm and the tibial radius 330 is approximately 28 mm. The central concave radius 340 of the femoral component 110 is approximately 13 mm and the corresponding radius 350 of the tibial component 120 is approximately 11 mm. The height 360 of the patella bearing surface 125 from the distal extreme of the condyles 300 is approximately 7 mm. The surface 305 connecting the patella bearing surface 125 with the distal extreme of the condyles 300 slopes at an angle of approximately 23 degrees with respect to a transverse plane 315.

Figure 14:
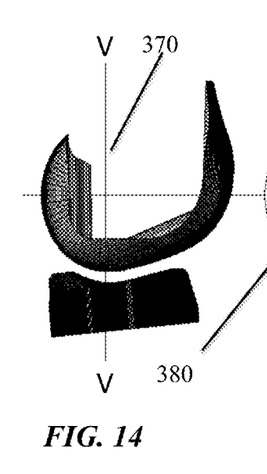
FIG. 14 is a sagittal view of embodiments of the femoral and tibial components and indicates the vertical axis of the tibia.
Figures 16, 17:
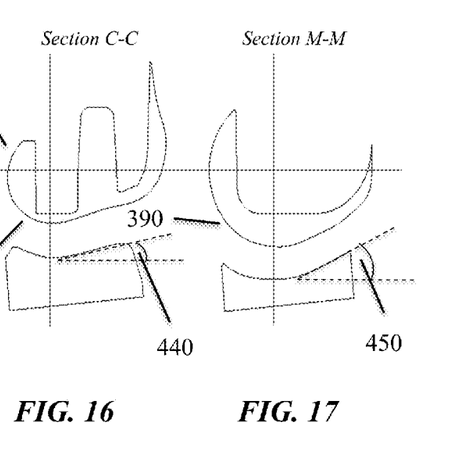
FIG. 16 is a sagittal view of section C-C of embodiments of the femoral and tibial components.
FIG. 17 is a sagittal view of section M-M of embodiments of the femoral and tibial components.

FIG. 14 is a sagittal view of the femoral 110 and tibial 120 components and indicates the vertical axis V-V 370. FIGS. 15, 16, and 17 provide cross sectional cuts for the cutting planes 220, C-C 230, and M-M 240 respectively. For clarity, the tibial component 120 has been lowered in relation to the femoral component 110. The posterior segment of the lateral condyle cross sectional cut L-L 380 and the posterior segment of the medial condyle cross sectional cut M-M 390 have a constant radius of approximately 23 mm. The anterior segment of the lateral tibial component cross sectional cut L-L exhibits an approximately linear slope 430 of approximately 7 degrees descending in the anterior to posterior direction. All angles of slope are relative to a transverse plane. The corresponding segment of the femoral component exhibits an approximately linear slope 420 of approximately 12 degrees descending in the anterior to posterior direction. The anterior segment of the central tibial component cross sectional cut C-C exhibits an approximately linear slope 440 of approximately 12 degrees descending in the anterior to posterior direction. While the anterior segment of the medial tibial component cross sectional cut M-M exhibits an approximately linear slope 450 of approximately 20 degrees descending in the anterior to posterior direction. The furthest clockwise posterior segment of the central cross sectional cut C-C may be defined by a radius of approximately 14 mm smoothly transitioning to a radius of approximately 16 mm for the balance of the posterior segment. The posterior lips 250 on the lateral and medial tibial sections have radii of approximately 23 mm.

Figure 18:
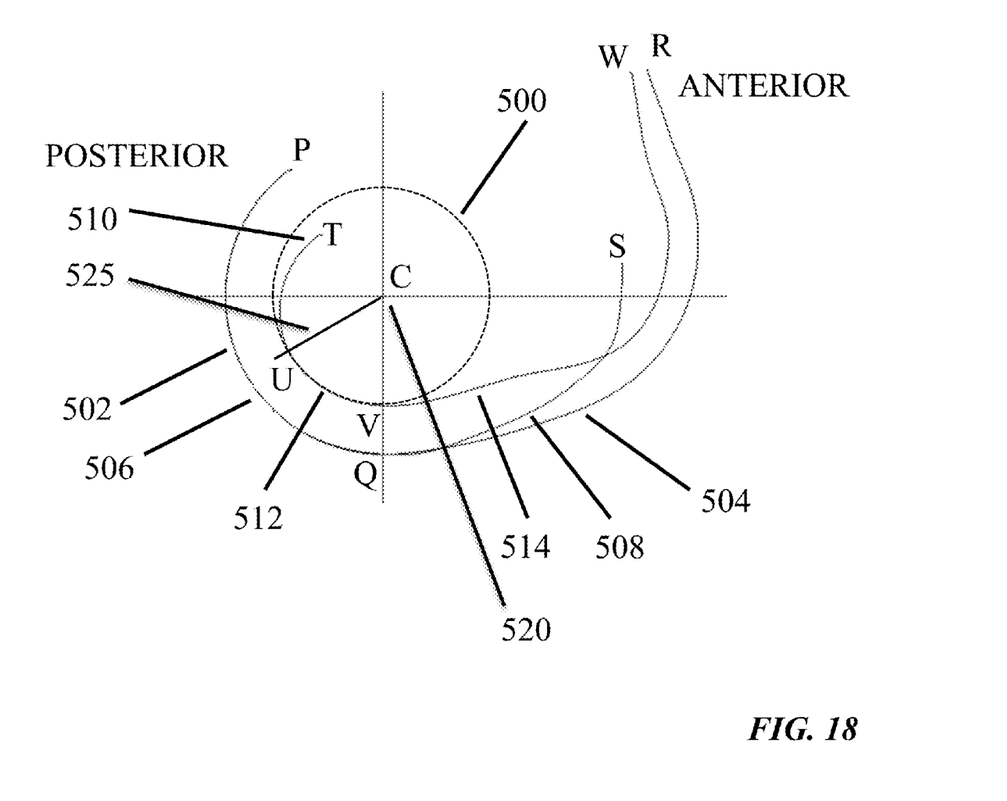
FIG. 18 is a sagittal view of the superimposed cross-sections of the femoral component.

The cross-sections of the bearing surfaces of femoral component are related. As shown in FIG. 18, which is a sagittal view of superimposed cross-sections L-L 220, C-C 230, and M-M 240, the centers of the posterior portions of the sections through the lateral and medial condyles and the center are collinear, in order to guide the motion effectively. The common center of circle 500 is C 520. The lateral cross-section is PQR 504. The medial cross-section is PQS 508. The center cross-section is TUVW 514. From P to Q, the posterior arc 502 of the lateral condyle 190 and the posterior arc 506 of the medial condyles 200 are coincident, with a center on C 520. Anterior to point Q, the cross-sections of the lateral 190 and medial condyles 200 diverge. From U to V 512, the center cross-section is an arc with a center on C 520, with the difference in the radii with the lateral and medial section being approximately the same depth as the patella groove, this depth being distance VQ. The line CU 525 is at 60 degrees to the vertical, so that point U will rotate to the lowest point V at 60 degrees flexion of the femoral component. However from U to T 510, the radius of the central section becomes progressively smaller. The shape of this curve causes the central bearing to remain in the same anterior-posterior position from 0 to 60 degrees flexion, but after 60 degrees flexion, the central section can move progressively posterior. The posterior motion is caused by the previously mentioned posterior slope of the lateral tibial surface, causing the lateral femoral surface to move down the slope under gravity.

STATEMENT REGARDING PREFERRED EMBODIMENTS

While the invention has been described with respect to the foregoing, those skilled in the art will readily appreciate that various changes and/or modifications can be made to the invention without departing from the spirit or scope of the invention as defined by the appended claims.

What is claimed is:

1. A total knee replacement comprising:
   a femoral component having a femoral bearing surface, said femoral bearing surface comprising a lateral section located adjacent, in a medial-lateral direction to an central section that is adjacent, in a medial-lateral direction, to a medial section,
      wherein coronal and sagittal cross-sections of said lateral and medial sections are convex, and central section has a convex sagittal cross section and a concave coronal cross section; and
   a tibial component with a tibial bearing, surface in articulating contact with said femoral bearing surface, said tibial bearing surface comprising a lateral segment located adjacent, in a medial-lateral direction, to an central segment that is adjacent, in a medial-lateral direction, to a medial segment,
      wherein sagittal cross section of said lateral segment is flat and corona cross section is concave, a sagittal and coronal cross sections of said medial segment are concave, and the sagittal cross section of the central segment is concave while the coronal, cross section is convex; and
      coronal cross-sections of said lateral sections are defined by a first radius, and coronal cross-sections of said lateral segments are defined by a second radius, said first radius is smaller than said second radius;
      coronal cross-sections of said medial sections are defined by a third radius, and coronal cross-sections of said lateral segments are defined by a fourth radius, said third radius is smaller than said fourth radius;
      sagittal cross-sections of said medial sections are defined by a fifth radius, and sagittal cross sections of said medial segments are defined by a sixth radius, said fifth radius is smaller than said sixth radius;
      sagittal cross-sections of said central sections are defined by a seventh radius, and sagittal cross-sections of said central segments are defined by a eighth radius, said seventh radius is smaller than said eighth radius; and
      coronal cross sections of said central sections are defined by a ninth radius, and sagittal cross-sections of said central segments are defined by a tenth radius, said tenth radius is smaller than said ninth radius.

2. The total knee replacement, in accordance with claim 1, wherein:
   said lateral section of said femoral component comprises lateral condyle and said medial section of said femoral component comprises a medial condyle, the sagittal cross section of each of said medial condyle and said lateral condyle has a constant sagittal radius over the arc of flexion from zero to approximately 160 degrees flexion, and from the anterior extreme, to the distal end for 0 degrees flexion, the sagittal section slopes upwards by an average of 12 degrees on the lateral side and 10 degrees on the medial side.

3. The total knee replacement, in accordance with claim 1, wherein:
   said sagittal cross-section of said flat lateral segment of said tibial component is sloped by approximately 7 degrees relative to a transverse plane descending in the posterior direction;
   said sagittal cross-section of said flat lateral section of said femoral component is sloped by approximately 12 degrees relative to a transverse plane descending in the posterior direction;
   said sagittal cross-section of said flat central segment of said tibial component is sloped posteriorly by approximately 12 degrees relative to a transverse plane descending in the posterior direction; and
   said sagittal cross section of said flat medial segment of said tibial component is sloped by approximately 20 degrees relative to a transverse plane descending in the posterior direction.

4. The total knee replacement, in accordance with claim 2, wherein a radius of a sagittal cross-section of a posterior lip of said tibial component is equal to, or up to 2 mm greater than, the radius of a cross-section of said femoral condyles.

5. The total knee replacement in accordance with claim 1, a patella bearing surface has a depth of at least 7 mm and a side slope angle of 23 degrees.

6. The total knee replacement, in accordance with claim 1, a patella bearing surface has a decreasing sagittal radius with increasing flexion angle front approximately 16 mm to 14 mm.

7. The total knee replacement, in accordance with claim 5, wherein said patella bearing surface is a replica of an anatomical patella flange, but is continued distally and posteriorly.

8. The total knee replacement, in accordance with claim 1, wherein a central region of said segment of the lateral tibial surface is sloped posteriorly in the sagittal plane by 5-8 degrees relative to a transverse plane and is configured to produce posterior femoral displacement by gravity.

9. The total knee replacement, in accordance with claim 1, wherein said femoral and tibial bearing surfaces are configured to guide motion, said motion comprising a posterior displacement of the lateral femoral condyle of 8-12 mm and a posterior displacement of the medial condyle of 2-4 mm.

10. The total knee replacement, in accordance with claim 1, that provides a greater lateral laxity than medial laxity.

11. The total knee replacement, in accordance with claim 1, where a lateral laxity is anteriorly greater than posteriorly, and a medial laxity is greater posteriorly than anteriorly.

12. The total knee replacement, in accordance with claim 1, wherein bearing surfaces of said central segment and said central section are configured to provide a total of 4-6 mm of posterior displacement of the femur on the tibia throughout flexion.

13. The total knee replacement, in accordance with claim 1, wherein said medial hearing surfaces limit anterior displacement of the femur on the tibia to 1-2 mm and limit posterior displacement to 2-4 mm.

14. The total knee replacement, in accordance with claim 1, comprising a continuous, patella groove on the femoral component configured so that the patella has full contact throughout a full flexion range.

* * * * *